US00PP17907P2

(12) United States Plant Patent
Anatriello

(10) Patent No.: US PP17,907 P2
(45) Date of Patent: Aug. 7, 2007

(54) ***EURYOPS* PLANT NAMED 'ATN CS5'**

(50) Latin Name: *Euryops pectinatus*
Varietal Denomination: ATN CS5

(76) Inventor: Lucilene Anatriello, Rua Carmelino Goncalves Condessa 320, 15020020 SP, Sao Jose do Rio Preto (BR)

( * ) Notice: Subject to any disclaimer, the term of this patent is extended or adjusted under 35 U.S.C. 154(b) by 0 days.

(21) Appl. No.: 11/366,064

(22) Filed: Mar. 2, 2006

(51) Int. Cl.
*A01H 5/00* (2006.01)

(52) U.S. Cl. ..... Plt./226

(58) Field of Classification Search ..... Plt./263, Plt./226

See application file for complete search history.

*Primary Examiner*—Anne Marie Grunberg
*Assistant Examiner*—S. B. McCormick-Ewoldt

(57) ABSTRACT

A new and distinct *Euryops* cultivar named 'ATN CS5' is disclosed, characterized by a compact plant habit, bright green foliage, yellow ray and disc florets and continuous flowering.

1 Drawing Sheet

Latin name of the genus and species: *Euryops pectinatus*.
Variety denomination: 'ATN CS5'.

BACKGROUND OF THE INVENTION

The new cultivar 'ATN CS5' was discovered as a whole plant mutation. The new cultivar was discovered as a single plant by Lucilene Anatriello in February 2004 in a cultivated area of São José do Rio Preto, Brazil. 'ATN CS5' was discovered growing in a field of *Euryops* 'Athena Sun'. The exact parents are unknown.

Asexual reproduction of the new cultivar 'ATN CS5' by vegetative cuttings was performed in São José do Rio Preto, Brazil, and has shown that the unique features of this new cultivar are stable and reproduced true to type on successive generations.

SUMMARY OF THE INVENTION

The cultivar 'ATN CS5' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'ATN CS5.' These characteristics in combination distinguish 'ATN CS5' as a new and distinct *Euryops* cultivar:

1. Compact plant form, including shorter overall plant height and shorter internode length.
2. Continuous flowering from March through October, with periods of less flowering every 6 to 8 weeks, followed by a new flush of highly floriferous branches
3. Bright green foliage
4. Yellow ray florets and a yellow disc
5. Shrubby, mounding plant habit.

Plants of the new cultivar 'ATN CS5' can be compared to *Euryops* 'Athena Sun'. Plants of the new cultivar 'ATN CS5' differ from 'Athena Sun' in the following characteristics:

1. 'ATN CS5' has a shorter over all plant height.
2. 'ATN CS5' has a shorter internode length.

3. 'ATN CS5' has lighter green foliage.
4. 'ATN CS5' has more persistent lower branches, with the foliage constantly growing near the ground.
5. 'ATN CS5' has a less woody main stem.

Plants of the new cultivar 'ATN CS5' can be also be compared to *Euryops* 'Munchkin.' Plants of the new cultivar 'ATN CS5' differ from 'Munchkin' in the following characteristics:

1. 'ATN CS5' has a shorter over all height and wider width.
2. 'ATN CS5' has a shorter internode length.
3. 'ATN CS5' has lighter green foliage.
4. 'ATN CS5' has more ray florets on each inflorescence.

BRIEF DESCRIPTION OF THE PHOTOGRAPH

The accompanying photograph in FIG. 1 illustrates in full color a typical plant of 'ATN CS5' grown in an outdoor garden. Rooted cuttings were planted in February and grown under outdoor conditions until September. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'ATN CS5' plants grown in Oxnard, Ventura County, Calif., during the month of February through August 2005. The growing temperature ranged from 12° C. to 15° C. at night to 12° C. to 35° C. during the day. Measurements and numerical values represent averages of typical flowering types.

Botanical classification: *Euryops pectinatus* cultivar 'ATN CS5'.

Commercial classification: Half hardy garden perennial.

PROPAGATION

Time to rooting: Approximately 28–35 days.
Root description: Semi-woody.

PLANT

Growth habit: Upright, mounding half-woody shrub.
Height: Approximately 31.8 cm.
Plant spread: Approximately 1.5 cm.
Growth rate: Moderate.
Branching characteristics: Free-branching.
Length of lateral branches: Approximately 17.8 cm.
Number of leaves per lateral branch: Approximately 125.
Age of plant described: Approximately 212 days.

FOLIAGE

Leaf:
*Arrangement.*—Opposite.
*Average length.*—Approximately 7.5 cm.
*Average width.*—Approximately 2.5 cm.
*Shape of blade.*—Oblanceolate with deep lobes.
*Apex.*—Cuspidate.
*Base.*—Acuminate.
*Attachment.*—Petiolate.
*Margin.*—Entire.
*Texture of top surface.*—Glabrous.
*Texture of bottom surface.*—Glabrous.
*Leaf internode length.*—Approximately 2 cm.
*Color.*—Young foliage upper side: Near R.H.S. Green 137B. Young foliage under side: Near Green 138B. Mature foliage upper side: Near Green 137A. Mature foliage under side: Near Green 137D.
*Venation.*—Type: Pinnately veined. Venation color upper side: Near Green 137A. Venation color under side: Near Green 137D.
Petiole:
*Average length.*—Approximately 0.4 cm.
*Color.*—Near Yellow-Green 145B.
*Diameter.*—Approximately 0.2 cm.

BLOOM

Inflorescence:
*Flowering habit.*—Continuous.
*Inflorescence form.*—Daisy.
*Natural flowering season.*—Approximately the first week of March through October.
*Number of inflorescences per lateral branch.*—Approximately 4.
*Inflorescence diameter.*—Approximately 3 cm.
*Disc diameter.*—Approximately 1 cm.
*Inflorescence depth.*—Approximately 0.6 cm.
*Inflorescence longevity on plant.*—Approximately 10 days.
*Persistence.*—Persistent.
Ray florets:
*Appearance.*—Matte.
*Texture.*—Ribbed.
*Average number of ray florets per inflorescence.*—20.
*Shape.*—Oblanceolate.
*Aspect.*—Slightly recurved.
*Margin.*—Entire.
*Apex.*—Retuse.
*Length.*—Approximately 1.5 cm.
*Width.*—Approximately 0.3 cm.
*Color.*—Upper surface at first opening: Near Yellow 13C. Upper surface at maturity: Near Yellow 13B. Upper surface at fading: Near Yellow 14C. Under surface at first opening: Near Yellow 13C. Under surface at maturity: Near Yellow 13B. Under surface at fading: Near Yellow 13C.
Disc florets:
*Appearance.*—Shiny.
*Texture.*—Smooth.
*Average number of florets per disc.*—Approximately 120.
*Shape.*—Tubular.
*Apex.*—Rounded.
*Average length.*—Approximately 0.03 cm.
*Average width.*—Approximately 0.05 mm.
*Color.*—At first opening: Near Yellow 13C. At maturity: Near Yellow-Orange 15A. At fading: Near Yellow-Orange 15B.
Peduncle:
*Length.*—At terminal end (shortest): Approximately 9.5 cm. At lateral end (longest): Approximately 15.5 cm.
*Angle to stem.*—Highly acute.
*Strength.*—Moderate.
*Color.*—Near Green 143C.
*Habit.*—Upright, straight.
*Diameter.*—Approximately 0.1 cm.
*Surface texture.*—Smooth.
Inflorescence bud:
*Length.*—Approximately 0.2 cm.
*Diameter.*—Approximately 0.5 cm.
*Form.*—Globular.
*Color.*—Near Green 142C.
Involucral bracts (phyllaries):
*Appearance.*—Matte.
*Texture.*—Smooth.
*Number.*—Approximately 10, fused.
*Shape.*—Lanceolate.
*Margin.*—Entire.
*Apex.*—Broadly acute.
*Length.*—Approximately 0.6 cm.
*Width.*—Approximately 0.2 cm.
*Color.*—Upper side: Near Yellow-Green 144C. Under side: Near Yellow-Green 144A.

REPRODUCTIVE ORGANS

Ray florets:
*Number of pistils per floret.*—1.
*Stigma shape.*—Bi-lobed.
*Stigma color.*—Near Yellow-Orange 14A.
*Style color.*—Near Yellow-Orange 16B.
*Style length.*—Approximately 0.04 cm.
Disc florets:
*Number of pistils per floret.*—1.
*Stigma shape.*—Bi-lobed.
*Stigma color.*—Near Yellow 13C.
*Style length.*—Approximately 0.3 cm.
*Style color.*—Near Yellow 12C.
*Number of stamens per floret.*—Approximately 5.
*Anther shape.*—Tubular.
*Anther color.*—Near Yellow-Orange 15A.
*Pollen color.*—Near Yellow-Orange 15A.

OTHER CHARACTERISTICS

Disease and pest resistance: Neither resistance nor susceptibility to common diseases and pests has been observed. Common pests are slugs, snails and thrips.

Drought tolerance/cold tolerance: Flowering plants are hardy to 22° F. and will freeze with a temperature of −5.0° C. *Euryops* is drought tolerant once established in the garden.

Fruit/seed production: Seed production is rare in this species and has not been observed in this variety to date.

What is claimed is:

1. A new and distinct cultivar of *Euryops* plant named 'ATN CS5' as herein illustrated and described.

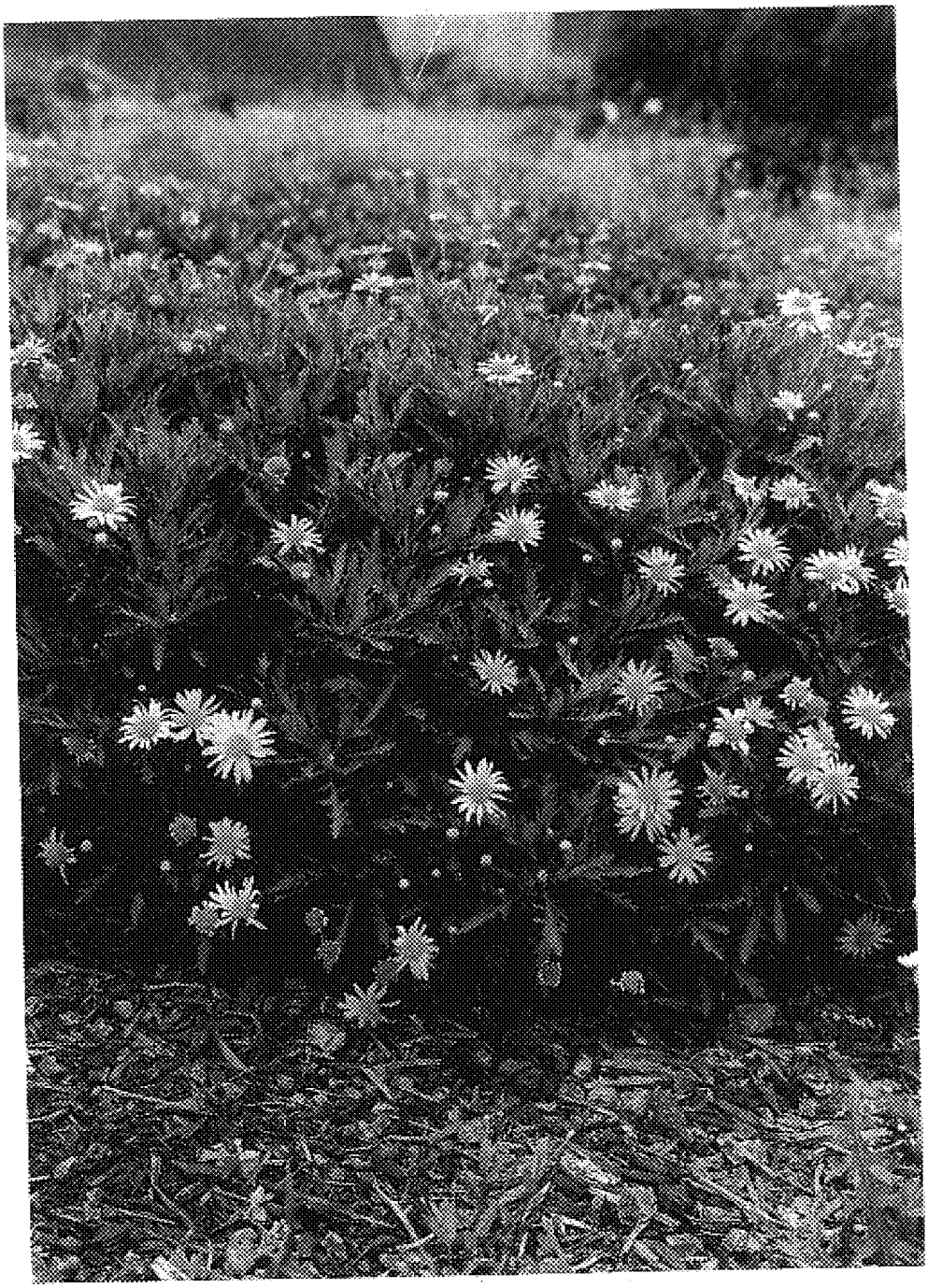

* * * * *